US00RE37406B1

(19) United States
(12) Reissued Patent
Behrmann et al.

(10) Patent Number: US RE37,406 E
(45) Date of Reissued Patent: Oct. 9, 2001

(54) SURFACE SUPPORTED COBALT CATALYSTS, PROCESS UTILIZING THESE CATALYSTS FOR THE PREPARATION OF HYDROCARBONS FROM SYNTHESIS GAS AND PROCESS FOR THE PREPARATION OF SAID CATALYSTS

(75) Inventors: William C. Behrmann; Kym B. Arcuri; Charles H. Mauldin, all of Baton Rouge, LA (US)

(73) Assignee: Exxon Research and Engineering Co., Florham Park, NJ (US)

(21) Appl. No.: 09/133,422

(22) Filed: Aug. 13, 1998

Related U.S. Patent Documents

Reissue of:
(64) Patent No.: 5,545,674
Issued: Aug. 13, 1996
Appl. No.: 08/377,293
Filed: Jan. 24, 1995

U.S. Applications:

(63) Continuation of application No. 08/243,436, filed on May 13, 1994, now abandoned, which is a continuation of application No. 08/032,916, filed on Mar. 18, 1993, now abandoned, which is a continuation-in-part of application No. 07/881,935, filed on May 11, 1992, now abandoned, which is a continuation of application No. 07/667,993, filed on Mar. 12, 1991, now abandoned, which is a continuation-in-part of application No. 07/310,258, filed on Feb. 13, 1989, now abandoned, which is a continuation-in-part of application No. 07/072,517, filed on Jul. 13, 1987, now abandoned, which is a continuation-in-part of application No. 07/046,649, filed on May 7, 1987, now abandoned.

(51) Int. Cl.[7] ..... C07C 27/06
(52) U.S. Cl. ..... 518/715
(58) Field of Search ..... 518/715

(56) References Cited

U.S. PATENT DOCUMENTS

| | | |
|---|---|---|
| 2,223,777 | 12/1940 | Beeck et al. . |
| 2,512,608 | 6/1950 | Buchmann . |
| 2,599,978 | 6/1952 | Davis et al. . |
| 2,865,868 | 12/1958 | McKinley et al. . |
| 3,799,887 | 3/1974 | Brennan . |
| 3,928,238 | 12/1975 | Koberstein et al. . |
| 3,998,759 | 12/1976 | Hoekstra . |
| 4,034,060 | 7/1977 | Koberstein et al. . |
| 4,051,072 | 9/1977 | Bedford et al. . |
| 4,255,285 | 3/1981 | Engelbach et al. . |
| 4,521,618 | 6/1985 | Arntz et al. . |
| 4,539,409 | 9/1985 | Arntz et al. . |
| 4,542,122 | 9/1985 | Payne et al. . |
| 4,547,486 | 10/1985 | Shyr . |
| 4,556,752 | 12/1985 | Mauldin et al. . |
| 4,568,663 | 2/1986 | Mauldin . |
| 4,595,703 | 6/1986 | Payne et al. . |
| 4,599,481 | 7/1986 | Post et al. . |
| 4,621,072 | 11/1986 | Arntz et al. . |
| 4,623,669 | 11/1986 | Meier et al. . |
| 4,637,993 | 1/1987 | van Erp et al. . |
| 4,663,305 | 5/1987 | Mauldin et al. . |
| 4,670,475 | 6/1987 | Mauldin . |
| 4,729,981 | 3/1988 | Kobylinski et al. . |
| 4,755,536 | 7/1988 | Mauldin et al. . |
| 4,794,099 | 12/1988 | Iglesia et al. . |
| 4,804,796 | 2/1989 | Wang et al. . |
| 4,857,559 | 8/1989 | Eri et al. . |
| 5,128,327 | 7/1992 | Behrmann et al. . |

FOREIGN PATENT DOCUMENTS

| | | |
|---|---|---|
| 2024246A | 1/1989 | (GB) . |

OTHER PUBLICATIONS

Everson, et al., "Fischer–Tropsch Reaction Studies with Supported Ruthenium Catalysts I. Product Distributions at Moderate Pressures and Catalyst Deactivation," Journal of Catalysis 53, 186–197 (1978).

Dixit, et al., "Kinetics of the Fischer–Tropsch Synthesis," Industrial Engineering Chemical Process Des. Dev. 1983, 22, pp. 1–9.

*Primary Examiner*—Laura L. Stockton
(74) *Attorney, Agent, or Firm*—Jay Simon

(57) ABSTRACT

A supported particulate cobalt catalyst is formed by dispersing cobalt, alone or with a metal promoter, particularly rhenium, as a thin catalytically active film upon a particulate support, especially a silica or titania support. This catalyst can be used to convert an admixture of carbon monoxide and hydrogen to a distillate fuel constituted principally of an admixture of linear paraffins and olefins, particularly a $C_{10+}$ distillate, at high productivity, with low methane selectivity. A process is also disclosed for the preparation of these catalysts.

29 Claims, 3 Drawing Sheets

SURFACE SUPPORTED COBALT CATALYSTS, PROCESS UTILIZING THESE CATALYSTS FOR THE PREPARATION OF HYDROCARBONS FROM SYNTHESIS GAS AND PROCESS FOR THE PREPARATION OF SAID CATALYSTS

Matter enclosed in heavy brackets [ ] appears in the original patent but forms no part of this reissue specification; matter printed in italics indicates the additions made by reissue.

CROSS REFERENCE TO RELATED APPLICATIONS

This application is *RE of U.S. application Ser. No. 08/377, 293 filed Jan. 24, 1995 abn., which is* a continuation of U.S. application Ser. No. 08/243,436 filed May 13, 1994, *which is a continuation of U.S. application Ser. No. 08/032,916 Mar. 18, 1993 ABN*, which is a continuation-in-part of U.S. Ser. No. 881,935, filed May 11, 1992, which was a Rule 60 Continuation of U.S. Ser. No. 667,993, filed Mar. 12, 1991, which was a continuation-in-part of U.S. Ser. No. 310,258, filed Feb. 13, 1989, which was a continuation-in-part of U.S. Ser. No. 072,517, filed Jul. 13, 1987, which was a continuation-in-part of U.S. Ser. No. 046,649, filed May 7, 1987 all abandoned.

BACKGROUND AND PROBLEMS

1. Field of the Invention

This invention relates to catalyst compositions, process wherein these compositions are used for the preparation of liquid hydrocarbons from synthesis gas, and process for the preparation of said catalysts. In particular, it relates to catalysts, and process wherein $C_{10+}$ distillate fuels, and other valuable products, are prepared by reaction of carbon monoxide and hydrogen over cobalt catalysts wherein the metal is dispersed as a thin film on the outside surface of a particulate carrier, or support, especially a titania carrier, or support.

2. The Prior Art

Particulate catalysts, as is well known, are normally formed by dispersing catalytically active metals, or the compounds thereof upon carriers, or supports. Generally, in making catalysts the objective is to disperse the catalytically active material as uniformly as possible throughout a particulate porous support, this providing a uniformity of catalytically active sites from the center of a particle outwardly.

Catalysts have also been formed by dispersing catalytically active materials upon dense support particles; particles impervious to penetration by the catalytically active materials. Ceramic or metal cores have been selected to provide better heat transfer characteristics, albeit generally the impervious dense cores of the catalyst particles overconcentrates the catalytically active sites within a reduced reactor space and lessens the effectiveness of the catalyst. Sometimes, even in forming catalysts from porous support particles greater amounts of the catalytic materials are concentrated near the surface of the particles simply because of the inherent difficulty of obtaining more uniform dispersions of the catalytic materials throughout the porous support particles. For example, a catalytic component may have such strong affinity for the support surface that it tends to attach to the most immediately accessible surface and cannot be easily displaced and transported to a more central location within the particle. Catalyst dispersion aids, or agents are for this reason often used to overcome this effect and obtain better and more uniform dispersion of the catalytically active material throughout the catalyst particles.

Fischer-Tropsch synthesis for the production of hydrocarbons from carbon monoxide and hydrogen is now well known, and described in the technical and patent literature. The earlier Fischer-Tropsch catalysts were constituted for the most part of non-noble metals dispersed throughout a porous inorganic oxide support. The Group VIII non-noble metals, iron, cobalt, and nickel have been widely used in Fischer-Tropsch reactions, and these metals have been promoted with various other metals, and supported in various ways on various substrates, principally alumina. Most commercial experience, however, has been based on cobalt and iron catalysts. The first commercial Fischer-Tropsch operation utilized a cobalt catalyst, though later more active iron catalysts were also commercialized. The cobalt and iron catalysts were formed by compositing the metal throughout an inorganic oxide support. An important advance in Fischer-Tropsch catalysts occurred with the use of nickel-thoria on kieselguhr in the early thirties. This catalyst was followed within a year by the corresponding cobalt catalyst, 100 Co:18 $ThO_2$:100 kieselguhr, parts by weight, and over the next few years by catalysts constituted of 100 Co:18 $ThO_2$:200 kieselguhr and 100 Co:5 $ThO_2$:8 MgO:200 kieselguhr, respectively. These early cobalt catalysts, however, are of generally low activity necessitating a multiple staged process, as well as low synthesis gas throughput. The iron catalysts, on the other hand, are not really suitable for natural gas conversion due to the high degree of water gas shift activity possessed by iron catalysts. Thus, more of the synthesis gas is converted to carbon dioxide in accordance with the equation: $H_2+2CO \rightarrow (CH_2)_x+CO_2$; with too little of the synthesis gas being converted to hydrocarbons and water as in the more desirable reaction, represented by the equation: $2H_2+CO \rightarrow (CH_2)_x+H_2O$.

U.S. Pat. No. 4,542,122 by Payne et al, which issued Sep. 17, 1985, describes improved cobalt catalyst compositions useful for the preparation of liquid hydrocarbons from synthesis gas. These catalyst compositions are characterized, in particular, as cobalt-titania or thoria promoted cobalt-titania, wherein cobalt, or cobalt and thoria, is composited or dispersed upon titania, or titania-containing support, especially a high rutile content titania. U.S. Pat. No. 4,568,663 by Mauldin, which issued Feb. 4, 1986, also discloses cobalt-titania catalysts to which rhenium is added to improve catalyst activity, and regeneration stability. These catalysts have performed admirably well in conducting Fischer-Tropsch reactions, and in contrast to earlier cobalt catalysts provide high liquid hydrocarbon selectivities, with relatively low methane formation.

Recent European Publication 1 178 008 (base on Application No. 85201546.0, filed: Sep. 25, 1985) and European Publication 0 174 696 (based on Application No. 852011412.5, filed: May 5, 1985), having priority dates Apr. 4, 1984 NL 8403021 and 13.09.84 NL 8402807, respectively, also disclose cobalt catalysts as well as a process for the preparation of such catalysts by immersion of a porous carrier once or repetitively within a solution containing a cobalt compound. The cobalt is dispersed over the porous carrier to satisfy the relation $\Sigma V_p/\Sigma V_c \leqq 0.85$ and $\Sigma V_p/\Sigma V_c \leqq 0.55$, respectively, where $\Sigma V_c$ represents the total volume of the catalyst particles and $\Sigma V_p$ the peel volumes present in the catalyst particles, the catalyst particles being regarded as constituted of a kernel surrounded by a peel. The kernal is further defined as one of such shape that at every point of the kernal perimeter the shortest distance (d) to the perimeter of the peel is the same, d being equal for all particles under consideration, and having been chosen such that the quantity of cobalt present in $\Sigma V_p$ is 90% of the quantity of cobalt present in $\Sigma V_c$. These particular catalysts, it is disclosed, show higher $C_{5+}$ selectivities than catalysts otherwise similar except that the cobalt component thereof is homogeneously distributed, or uniformly dispersed, throughout the carrier. Suitable porous carriers are disclosed as silica, alumina, or silica-alumina, and of these silica is preferred. Zirconium, titanium, chromium and ruthenium are disclosed as preferred of a broader group of promoters. Albeit these catalysts may provide better selectivities in synthesis gas conversion reactions vis-a-vis catalysts otherwise similar except the cobalt is uniformly dispersed throughout the carrier, like other cobalt catalysts disclosed in the prior art, the intrinsic activities of these catalysts are too low as a consequence of which higher temperatures are required to obtain a productivity which is desirable for commercial operations. Higher temperature operation, however, leads to a corresponding increase in the methane selectivity and a decrease in the production of the more valuable liquid hydrocarbons.

Productivity, which is defined as the standard volumes of carbon monoxide converted/volume catalyst/hour, is, of course, the life blood of a commercial operation. High productivities are essential in achieving commercially viable operations. However, it is also essential the high productivity be achieved without high methane formation, for methane production results in lower production of liquid hydrocarbons. Accordingly, an important and necessary objective in the production and development of catalysts is to produce catalysts which are capable of high productivity, combined with low methane selectivity.

Despite improvements, there nonetheless remains a need for catalysts capable of increased productivity, without increased methane selectivity. There is, in particular, a need to provide further improved catalysts, and process for the use of these catalysts in synthesis gas conversion reactions, to provided further increased liquid hydrocarbon selectivity, especially $C_{10+}$ liquid hydrocarbon selectivity, with further reduced methane formation.

3. Objects

It is, accordingly, the primary objective of this invention to fill this and other needs.

It is, in particular, an object of this invention to provide further improved, novel supported cobalt catalyst compositions, and process utilizing such compositions for the conversion of synthesis gas at high productivity, and low methane selectivity, to high quality distillate fuels characterized generally as $C_{10+}$ linear paraffins and olefins.

A further and more particular object is to provide novel, supported cobalt catalyst compositions, both promoted and unpromoted which approach, or meet the activity, selectivity and productivity of powdered catalysts but yet are of a size acceptable for commercial synthesis gas conversion operation.

A further object is to provide a process utilizing such catalyst compositions for the production from synthesis gas to $C_{10+}$ linear paraffins and olefins, at high productivity with decreased methane selectivity.

Yet another object i s to provide a process for the preparation of such catalysts.

4. The Invention

These objects and others are achieved in accordance with this invention embodying a supported particulate cobalt catalyst formed by dispersing the cobalt as a thin catalytically active film upon the surface of a particulate support, preferably silica or titania or titania-containing support, especially one wherein the rutile:anatase ratio of a titania support is at least about 3:2. This catalyst can be used to produce, by contact and reaction at reaction conditions with an admixture of carbon monoxide and hydrogen, a distillate fuel constituted principally of an admixture of linear paraffins and olefins, particularly a $C_{10+}$ distillate, preferably $C_{20+}$, at high productivity, with low methane selectivity. This product can be further refined and upgraded to high quality fuels, and other products such as mogas, diesel fuel and jet fuel, especially premium middle distillate fuels of carbon numbers ranging from about $C_{10}$ to about $C_{20}$.

In accordance with this invention the catalytically active cobalt component is dispersed and supported upon a particulate refractory inorganic oxide carrier, or support as a thin catalytically active surface layer, ranging in thickness from less than about 200 microns, preferably about 5–200 microns, with the loading of the cobalt, expressed as the weight metallic cobalt per packed bulk volume of catalyst, being sufficient to achieve the productivity required for viable commercial operations, e.g., a productivity in excess of about 150 $hr^{-1}$ at 200° C. The cobalt loading that achieves this result is at least about 0.04 grams (g) per cubic centimeter (cc), preferably at least about 0.05 g/cc in the rim also referred to as the thin catalytically active surface layer or film. Higher levels of cobalt tend to increase the productivity further and an upper limit of cobalt loading is a function of cobalt cost, diminishing increases in productivity with increases in cobalt, and ease of depositing cobalt. A suitable range may be from about 0.04 g/cc to about 0.7 g/cc, preferably 0.05 g/cc to about 0.7 g/cc in the rim, and more preferably 0.05 g/cc to 0.09 g/cc. Suitable supports are, e.g., silica, silica-alumina and alumina; and silica or titania or titania-containing support is preferred, especially a titania wherein the rutile:anatase ratio is at least about 3:2. The support makes up the predominant portion of the catalyst and is at least about 50 wt % thereof, preferably at least about 75 wt % thereof. The feature of a high cobalt metal loading in a thin catalytically active layer located at the surface of the particles, while cobalt is substantially excluded from the inner surface of the particles (the catalyst core should have <0.04 g/cc of active cobalt), is essential in optimizing the activity, selectivity and productivity of the catalyst in producing liquid hydrocarbons from synthesis gas, while minimizing methane formation.

Metals such as rhenium, zirconium, hafnium, cerium, thorium and uranium, or the compounds thereof, can be added to cobalt to increase the activity and regenerability of the catalyst. Thus, the thin catalytically active layers, rims, or films, formed on the surface of the support particles, especially the titania or titania containing support particles, can include in addition to a catalytically active amount of cobalt, any one or more of rhenium, zirconium, hafnium, cerium, uranium, and thorium, or admixtures of these with each other or with other metals or compounds thereof. Preferred thin catalytically active layers, rims, or films, supported on a support, notably a titania or a titania-containing support, thus include cobalt-rhenium, cobalt-zirconium, cobalt-hafnium, cobalt-cerium, cobalt-uranium, and cobalt-thorium, with or without the additional presence of other metals or compounds thereof.

Figure 2:
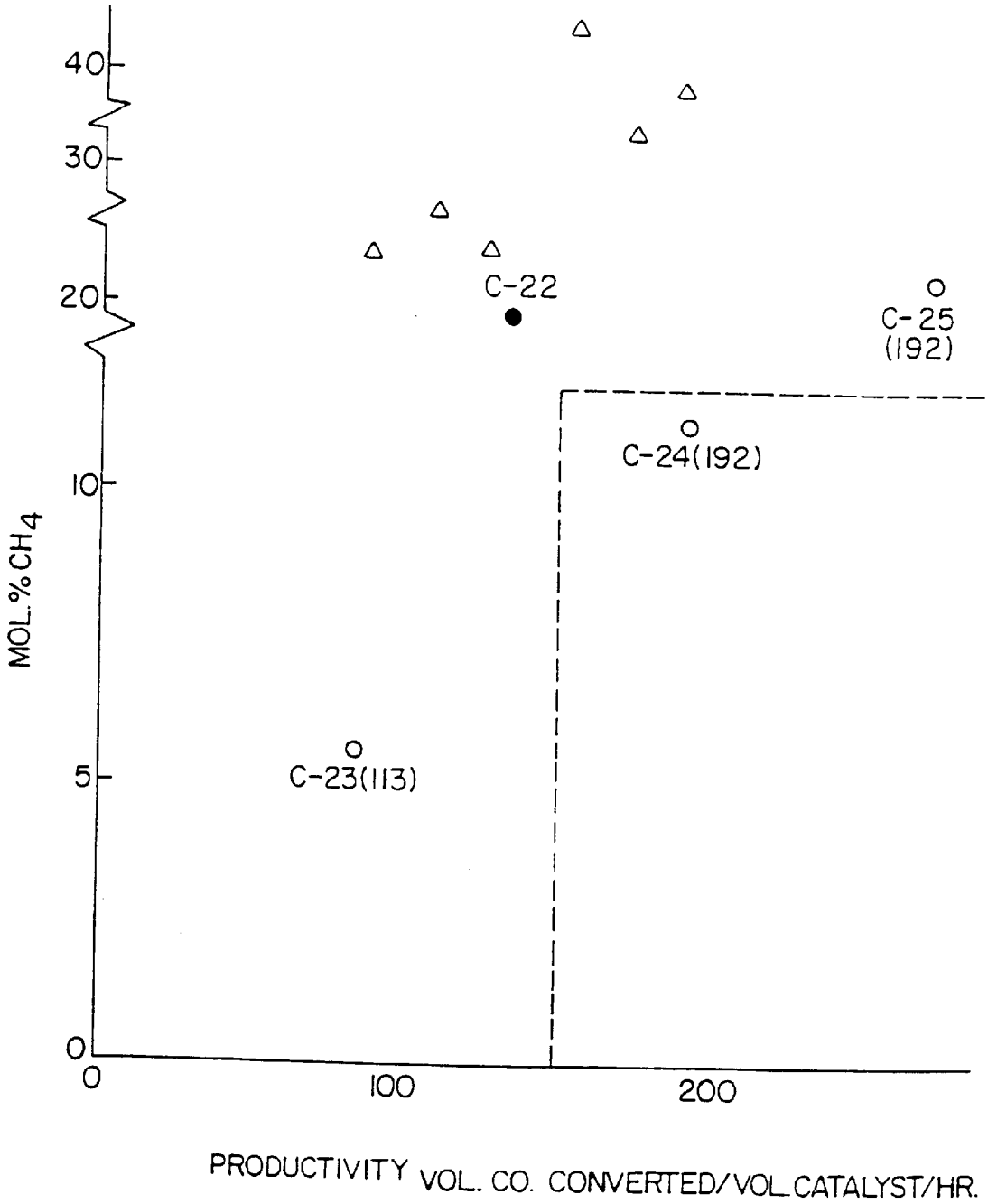

FIG. 2 is a similar plot of methane yield in the hydrocarbon synthesis product against productivity. The closed circle denotes a uniformly impregnated sphere, the open circle a rim or outer layer impregnated sphere with rim thickness indicated parenthetically; the trianglesydenoting data from EPA 178008.

Figure 3:
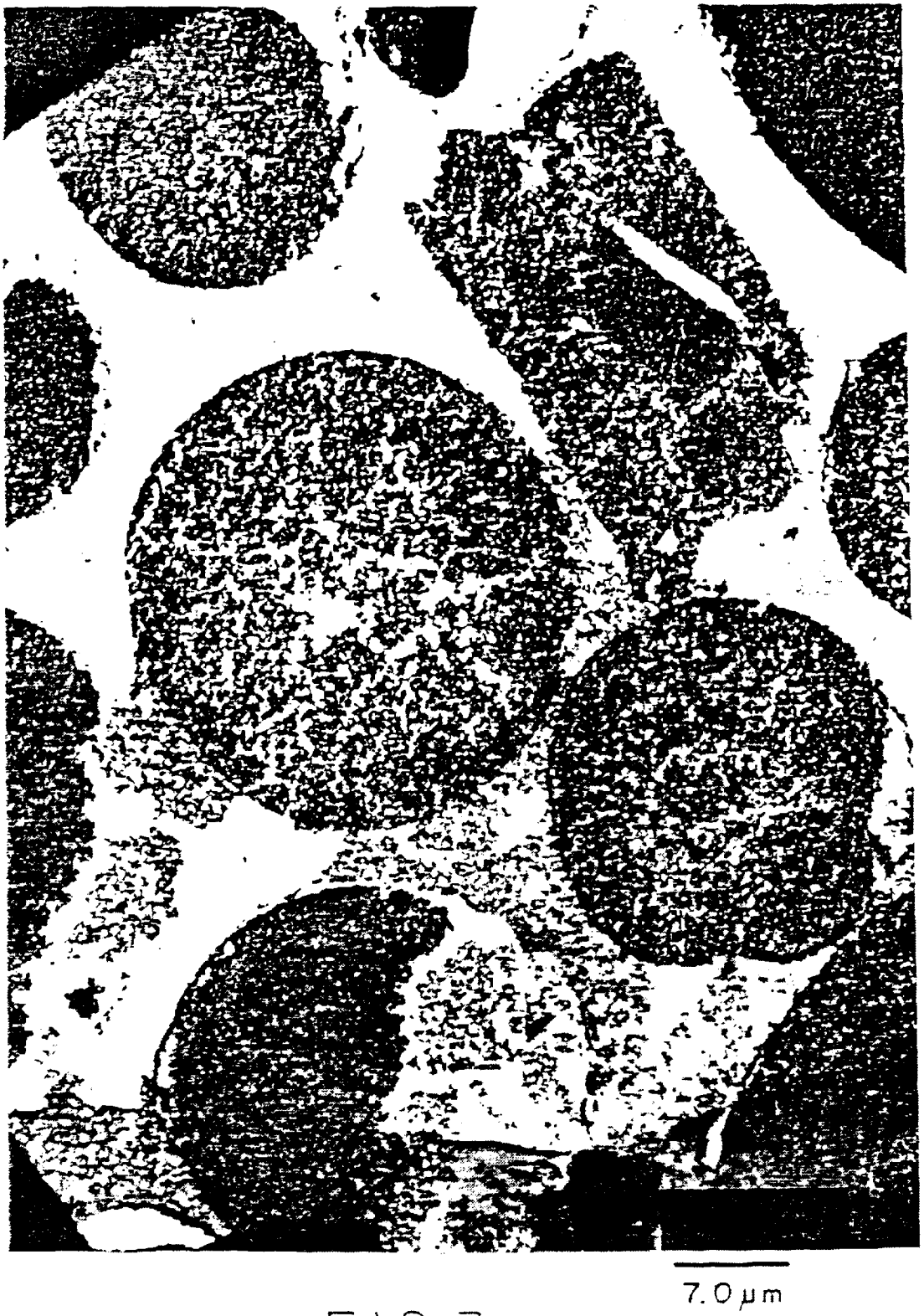

FIG. 3 shows high resolution imaging and EDS analysis of a cross-sectional view of a microtomed sample revealing the presence of an outer layer, approximately 0.5 $\mu$m thick, and rich in Al, Co and Re on catalyst pellets of ~10 to 100 micron sizes. Imaging and compositional analysis showed that the outermost 50 nm of this layer was highly enriched in Al, Co and Re.

A particularly preferred catalyst is one wherein the cobalt, or the cobalt and a promoter, is dispersed as a thin catalytically active film upon titania. $TiO_2$, or a titania-containing carrier, or support, in which the titania has a rutile::anatase weight ratio of at least about 3:2, as determined by ASTM D 3720-78; Standard Test Method for Ratio of Anatase to Rutile In Titanium Dioxide Pigments By Use of X-Ray Diffraction. Generally, the catalyst is one wherein the titania has a rutile:anatase ratio ranging at least about 3:2 to about 100:1, or greater, and more preferably from about 4:1 to about 100:1, or greater. Where any one of rhenium, zirconium, hafnium, cerium, thorium, or uranium metals, respectively, is added to the cobalt as a promoter to form the thin catalytically active film, the metal is added to the cobalt in concentration sufficient to provide a weight ratio of cobalt:metal promoter ranging from about 30:1 to about 2:1, preferably from about 20:1 to about 5:1. Rhenium and hafnium are the preferred promoter metals, rhenium being more effective in promoting improved activity maintenance on an absolute basis, with hafnium being more effective on a cost-effectiveness basis. These catalyst compositions, it has been found, produce at high productivity, with low methane selectivity, a product which is predominantly $C_{10+}$ linear paraffins and olefins, with very little oxygenates. These catalysts also provide high activity, high selectivity and high activity maintenance in the conversion of carbon monoxide and hydrogen to distillate fuels.

The cobalt catalysts of this invention, as contrasted with (i) cobalt catalysts, the cobalt portion of which is uniformly distributed throughout the support particles or (ii) cobalt catalysts having a relatively thick surface layer of cobalt on the support particles, have proven especially useful for the preparation of liquid hydrocarbons from synthesis gas at high productivities, with low methane formation. In contrast with the catalysts of this invention, the prior art catalysts are found to have lower activity, and especially poorer selectivity due to severe diffusion limitations. These catalysts (i) and (ii), supra, at high productivities, produce altogether too much methane. As productivity is increased to produce greater conversion of the carbon monoxide to hydrocarbons, increased amounts of methane are concurrently produced. It was thus found that increased productivity with these catalysts could only be obtained at the cost of increased methane formation. This result occurs, it is believed, because the carbon monoxide and hydrogen reactants all too slowly diffuse through the pores of the particulate catalyst which becomes filled with a liquid product, this resulting in underutilization of the catalytically active sites located within the interior of the particles. Both hydrogen and carbon monoxide must thus diffuse through the product-liquid filled pores, but hydrogen diffuses through the pores at a greater rate of speed than the carbon monoxide. Since both the hydrogen and the carbon monoxide are reacting at the catalytic sites at an equivalent rate, a high $H_2$/CO ratio is created in the interior of the particle which leads to high methane formation. As the rate of reaction is increased, e.g., by incorporating higher intrinsic activity or by operating at higher temperature, the catalyst becomes more limited by the rate of diffusion of the reactants through the pores. Selectivities are especially poor under the conditions of high productivity. Thus, the catalyst used during a Fischer-Tropsch hydrocarbon synthesis reaction is one the pores of which become filled with the product liquid. When the CO and $H_2$ are passed over the bed of catalyst and consumed at a rate which is faster than the rate of diffusion, $H_2$ progresses to the interior of the particle to a much greater extent than the CO, leaving the interior of the particles rich in $H_2$, and deficient in CO. The formation of methane within the particle interior is thus favored due to the abnormally high $H_2$/CO ratio; an unfavorable result since $CH_4$ is not a desirable product. The extent to which selectivity is debited depends on the magnitude of the difference between the rate of diffusion and the rate of reaction, i.e., the productivity.

The catalyst of this invention is thus one wherein essentially all of the active cobalt is deposited on the surface of the support particles, notably the titania or titania-containing support particles, while cobalt is substantially excluded from the inner surface of the particles. The surface film of cobalt must be very thin and contain an adequate loading of cobalt to maximize reaction of the hydrogen and carbon monoxide at the surface of the catalytic particle. The surface film of cobalt as stated thus ranges generally from about 5 microns to about 200 microns, preferably from about 40 microns to about 200 microns, with cobalt loadings of at least about 0.04 g/cc in the catalyst rim, preferably at least about 0.05 g/cc, more preferably ranging from about 0.04 g/cc to about 0.7 g/cc, still more preferably from about 0.05 g/cc to about 0.7 g/cc, and even more preferably ranging from about 0.05 g/cc to about 0.09 g/cc, calculated as metallic cobalt per pack bulk volume of catalyst. The promoter metal to be effective must also be contained within the surface film of cobalt. If extended into the interior of the particle outside the cobalt film the promoter metal will have little promotional effect, if any. The metal promoter should thus also be concentrated within the cobalt film at the surface of the catalyst, with the weight ratio of cobalt:metal promoter, as suggested, ranging from about 30:1 to about 2:1, preferably from about 20:1 to 5:1. The thickness of the surface metal film can be conveniently measured by an Electron Probe Analyzer, e.g., one such as produced by the JEOL Company, Model No. JXA-50A. Cross-sections of the catalyst particles of this invention measured via use of this instrument show very high peaks, or shoulders, at the edges of the particle across the line of sweep representative of cobalt concentration, with little or no cobalt showing within the particle interior. The edge, or "rim" of the "radially impregnated catalyst" will thus contain essentially all of the cobalt added to the catalyst. The thickness of the film, or rim, is unrelated to the absolute size, or shape of the support particles. Virtually any size particle can be employed as is normally employed to effect catalyst reactions of this type, the diameter of the particle ranging generally from about >10 microns to about 10 mm. For example, for a fixed-bed process, particle size may range from about 1 mm to 10 mm and for fluidized-bed processes such as slurry-bed, ebulating-bed and fluid-bed processes from about >10 microns to about 1 mm. In a fixed-bed process, particle size is dictated by pressure considerations. To reduce diffusion limitation effects even further, particle diameters are preferably less than 2 mm. The particles can be of virtually any shape, e.g., as is normally employed to effect reactions for this type, viz., as beads or spheres, extrudates, saddles or the like. By concentrating the catalytic metal, or metals, on the extreme outer surface of the particles, the normal diffusion limitation of the catalyst can be overcome. This new catalyst is more active in its function of bringing about a reaction between the CO and $H_2$. The catalyst because of its having the thin layer of catalytically active metal on its surface is in effect found to behave more ideally, approaching, in fact, the behavior of a powdered catalyst which is not diffusion limited. However, unlike in the use of powdered catalysts the flow of the reactants through the catalyst bed, because of the larger particle size of the catalyst, is virtually unimpeded. Higher productivity, with lower methane selectivity is the result; a result of considerable commercial consequence. At productivities greater than 150 $hr^{-1}$ (standard volumes of carbon monoxide converted per volume of catalyst per hour), notably from about 150 $hr^{-1}$, preferably above about 200 $hr^{-1}$, at 200° C. less than 15 mole percent of the carbon monoxide converted is converted to methane, preferably less than 10 mole % converted to methane.

The catalyst of the present invention can be used in fixed-bed, slurry-bed, ebulating-bed, and fluid-bed processes. Generally the catalyst will achieve a productivity of at least 150 $hr^{-1}$ at 200° C. for fixed-bed processes and at least about 1000 $hr^{-1}$ at 200° C. in other than fixed-bed processes (slurry-bed, ebulating-bed and fluid-bed). The processes are limited only by the ability to remove excess heat.

In conducting synthesis gas reactions the total pressure upon the CO and $H_2$ reaction mixture is generally maintained above about 80 psig, and preferably above about 140 psig. It is generally desirable to employ carbon monoxide, and hydrogen, in molar ratio of $H_2$:CO above about 0.5:1 and preferably equal to or above about 1.7:1 to increase the concentration of $C_{10+}$ hydrocarbons in the product. Suitably, the $H_2$:CO molar ratio ranges from about 0.5:1 to about 4:1, and preferably the carbon monoxide and hydrogen are employed in molar ratio $H_2$:CO ranging from about 1.7:1 to about 2.5:1. In general, the reaction is carried out at gas hourly space velocities ranging from about 100 V/Hr/V to about 5000 V/Hr/V, preferably from about 300 V/Hr/V to about 2000 V/Hr/V, measured as standard volumes of the gaseous mixture of carbon monoxide and hydrogen (0° C., 1 Atm.) per hour per volume of catalyst. The reaction is conducted at temperatures ranging from about 160° C. to about 290° C., preferably from about 190° C. to about 260° C., and more preferably about 190° C. to about 220° C. Pressures preferably range from about 80 psig to about 600 psig, more preferably from about 140 psig to about 400 psig. The product generally and preferably contains 60 percent, or greater, and more preferably 75 percent, or greater, $C_{10+}$ liquid hydrocarbons which boil about 160° C. (320° F.).

The catalysts employed in the practice of this invention can be prepared by spray techniques where a dilute solution of a cobalt compound, along or in admixture with a promoter metal compound, or compounds, as a spray is repetitively contacted with the hot support particles, e.g., silica, titania, or titania-containing support particles. The particulate support is maintained at temperatures equal to or above about 140° C. when contacted with the spray, and suitably the temperature of the support ranges from about 140° C. up to the decomposition temperature of the cobalt compound, or compounds in admixture therewith; preferably from about 140° C. to about 190° C. The cobalt compound employed in the solution can be any organometallic or inorganic compound which decomposes to give cobalt oxide upon initial contact or upon calcination, such as cobalt nitrate, cobalt acetate, cobalt acetylacetonate, cobalt naphthenate, cobalt carbonyl, or the like. Cobalt nitrate is especially preferred while cobalt halide and sulfate salts should generally be avoided. The cobalt salts may be dissolved in a suitable solvent, e.g., water, organic or hydrocarbon solvent such as acetone, methanol, pentane or the like. The total amount of solution used should be sufficient to supply the proper catalyst loading, with the film being built up by repetitive contacts between the support and the solvent. The preferred catalyst is one which consists essentially of cobalt, or cobalt and promoter, dispersed upon the titania, or titania-containing support, especially a rutile support. Suitably, the hot support, notably the titania support, is contacted with a spray which contains from about 0.05 g of cobalt/ml of solution to about 0.25 g of cobalt/ml of solution, preferably from about 0.10 g of cobalt/ml of solution to about 0.20 g of cobalt/ml of solution (plus the compound containing the promoter metal, if desired), generally from at least about 3 to about 12 contacts, preferably from about 5 to about 8 contacts, with intervening drying and calcination steps being required to form surface films of the required thicknesses. The hot support, in other words, is spray-contacted in a first cycle which includes the spray contact per se with subsequent drying and calcination, a second cycle which includes the spray contact per se with subsequent drying and calcination, a third spray contact which includes the spray contact per se with subsequent drying and calcination, etc. to form a film of the required thickness and composition. The drying steps are generally conducted at temperatures ranging above about 20° C., preferably from about 20° C. to about 125° C., and the calcination steps at temperatures ranging above about 150° C., preferably from about 150° C. to about 300° C.

A preferred method for preparing the catalysts particles is described in Preparation of Catalysts IV, 1987, Elsevier Publishers, Amsterdam, in an article by Arntz and Prescher, p. 137, et seq.

Silica and titania are preferred supports. Titania is particularly preferred. It is used as a support, either along or in combination with other materials for forming a support. The titania used for the support is preferably one which contains a rutile:anatase ratio of at least about 3:2, as determined by x-ray diffraction (ASTM D 3720-78). The titania supports preferably contain a rutile:anatase ratio of from about 3:2 to about 100:1, or greater, more preferably from about 4:1 to about 100:1, or greater. The surface area of such forms of titania are less than about 50 $m^2/g$. These weight concentrations of rutile provide generally optimum activity, and $C_{10+}$ hydrocarbon selectivity without significant gas and $CO_2$ make.

The prepared catalyst as a final step is dried by heating at a temperature above about 20° C., preferably between 20° C. and 125° C., in the presence of nitrogen or oxygen, or both, in an air stream or under vacuum. It is necessary to activate the catalyst prior to use. Preferably, the catalyst is contacted with oxygen, air, or other oxygen-containing gas at temperature sufficient to oxidize the cobalt and convert the cobalt to $Co_3O_4$. Temperatures ranging above about 150° C., and preferably above about 200° C. are satisfactory to convert the cobalt to the oxide, but temperatures above about 500° C. are to be avoided unless necessary for regeneration of a severely deactivated catalyst. Suitably, the oxidation of the cobalt is achieved at temperatures ranging from about 150° C. to about 300° C. The metal, or metals, contained on the catalyst are then reduced. Reduction is performed by contact of the catalyst, whether or not previously oxidized, with a reducing gas, suitably with hydrogen or hydrogen-containing gas stream at temperatures above about 200° C.; preferably above about 250° C. Suitably, the catalyst is reduced at temperatures ranging from about 200° C. to about 500° C. for periods ranging from about 0.5 to about 24 hours at pressures ranging from ambient to about 40 atmospheres. A gas containing hydrogen and inert components in admixture is satisfactory for use in carrying out the reduction.

The catalysts of this invention can be regenerated, and reactivated to restore their initial activity and selectivity after use by washing the catalyst with a hydrocarbon solvent, or by stripping with a gas. Preferably the catalyst is stripped with a gas, most preferably with hydrogen, or a gas which is inert or non-reactive at stripping conditions such as nitrogen, carbon dioxide, or methane. The stripping removes the hydrocarbons which are liquid at reaction conditions. Gas stripping can be performed at substantially the same temperatures and pressures at which the reaction is carried out. Pressures can be lower, however, as low as atmospheric or even a vacuum. Temperatures can thus range from about 160° C. to about 290° C., preferably from about 190° C. to about 260° C., and pressures from below atmospheric to about 600 psig, preferably from about 140 psig to about 400 psig. If it is necessary to remove coke from the catalyst, the catalyst can be contacted with a dilute oxygen-containing gas and the coke burned from the catalyst at controlled temperature below the sintering temperature of the catalyst. Most of the coke can be readily removed in this way. The catalyst is then reactivated, reduced, and made ready for use by treatment with hydrogen or hydrogen-containing gas with a fresh catalyst.

The invention will be more fully understood by reference to the following examples and demonstrations which present comparative data illustrating its more salient features.

The catalysts of this invention are disclosed in the following examples and demonstrations as Catalysts Nos. 14–21, and 24. These are catalysts which have surface films falling within the required range of thicknesses, and the surface film contains the required cobalt metal loadings. It will be observed that Catalysts No. 14–21 were formed by a process wherein a heated particulate $TiO_2$ substrate was repetitively contacted with a dilute spray solution containing both the cobalt and rhenium which was deposited as a thin surface layer, or film, upon the particles. Catalyst 24 was prepared similarly but with an $SiO_2$ particle. Catalysts Nos. 14–21 and 24 are contrasted in a series of synthesis gas conversion runs with Catalysts Nos. 1–8 and 22, catalysts wherein the metals are uniformly dispersed throughout $TiO_2$ or $SiO_2$ (No. 22) support particles, Catalysts Nos. 9–13, also "rim" catalysts but catalysts wherein the surface films, or rims, are too thick (Catalysts Nos. 11–13), however prepared, or do not contain an adequate cobalt metal loading within the surface film, or rim (Catalysts Nos. 9 and 23). Catalyst 25 is run at 220° C. for comparison with Catalyst 24. The higher temperature operation shows increased productivity but significantly higher methane production. It is clear that at high productivities the catalysts formed from the uniformly impregnated $TiO_2$ and $SiO_2$ spheres produce high methane. Moreover, even wherein a film of the catalytic metal is formed on the surface of the particles, it is essential that the surface film, or rim of cobalt be very thin and also contain an adequate loading of cobalt in the film. This is necessary to maximize reaction of the $H_2$ and CO at the surface of the particle wherein the cobalt metal reaction sites are located, while simultaneously reactions within the catalyst but outside the metal film or rim are suppressed to maximize productivity, and lower methane selectivity. The following data thus show that the catalysts of this invention, i.e., Catalysts Nos. 14–21 and 24 can be employed at productivities above 150 $hr^{-1}$, and indeed at productivities ranging above 150 $hr^{-1}$ to 200 $hr^{-1}$, and greater, to produce no more and even less methane than is produced by (i) catalysts otherwise similar except that the catalysts contain a thicker surface film, i.e., Catalysts Nos. 11–13, or (ii) catalysts which contain an insufficient cobalt metal loading with in a surface film of otherwise acceptable thinness, i.e., Catalyst Nos. 9 and 23. The data show that the catalysts of this invention at productivities ranging above about 150 $hr^{-1}$ to about 200 $hr^{31\ 1}$, and greater, at 200° C. can be employed to produce liquid hydrocarbons at methane levels well below 10 mole percent with $TiO_2$ and less than 15 mole percent with $SiO_2$.

EXAMPLES 1–8

A series of 21 different catalysts were prepared from titania. $TiO_2$, and 3 different catalysts from $SiO_2$, both supplied by a catalyst manufacturer in spherical form; the supports having the following physical properties, to wit:

$TiO_2$ (1 mm average diameter)
86–95% $TiO_2$ rutile content (by ASTM D 3720-78 test)
14–17 $m^2/g$ BET surface area
0.11–0.16 cc/g pore volume (by mercury intrusion).

| | |
|---|---|
| $SiO_2$ | 2.5 mm average diameter<br>244 $m^2/g$ BET surface area<br>0.96 cc/g pore volume (by nitrogen adsorption) |

In the catalyst preparations, portions of the $TiO_2$ spheres were impregnated with cobalt nitrate and perrhenic acid via several impregnation techniques as subsequently described. In each instance, after drying in vacuo at 125°–185° C., the catalysts were calcined in flowing air at 250°–500° C. for three hours. A first series of catalysts (Catalyst Nos. 1–8) were prepared wherein $TiO_2$ spheres were uniformly impregnated, and these catalysts then used in a series of base runs (Table 1). Catalyst Nos. 9–11 (Table 2) and 12–21 (Table 3) were prepared such that the metals were deposited on the outside surface of the spheres to provide a shell, film or rim. Catalysts Nos. 22–25 were prepared with 2.5 mm $SiO_2$ particles (Table 4). Catalyst No. 22 was a fully impregnated $SiO_2$ particle while Catalysts 23–25 were rim type catalysts prepared by spraying in a manner similar to that for Catalyst Nos. 14–21. Catalyst No. 23 had insufficient cobalt loading to produce adequate productivity. The thicknesses of the catalyst rim, or outer shell, were determined in each instance by Electron Microprobe Analysis. Runs were made with these catalysts each being contacted with synthesis gas at similar conditions and comparisons (except for Catalyst No. 25 run at 220° C.) then made with those employed to provide the base runs.

Catalyst Nos. 1–8, described in Table 1, were prepared as uniformly impregnated catalysts to wit: A series of uniformly impregnated $TiO_2$ spheres were prepared by immersing the $TiO_2$ spheres in acetone solutions of cobalt nitrate and perrhenic acid, evaporating off the solutions, and then drying and calcining the impregnated spheres. The Co and Re loadings, expressed as gms metal per cc of catalyst on a dry basis, deposited upon each of the catalysts are given in the second and third columns of Table 1.

Catalysts No. 9–11 were prepared to contain an outer rim or shell. These catalysts were prepared by a liquid displacement method which involves first soaking the $TiO_2$ in a water-immiscible liquid, draining off the excess liquid, and then dipping the wet spheres into a concentrated aqueous solution of cobalt nitrate (0.24 g Co/ml) and perrhenic acid (0.02 g Re/ml). Contact with the metal salt solution is limited to a very short period of time, during which the solution displaces the pre-soak liquid from the outer surface of the support particles. The rim-impregnated catalyst is quickly blotted on paper towels and dried in a vacuum oven at 140° C. Results are summarized in Table 2. The second column of Table2 thus identifies the presoak liquid, the third column the displacement time in minutes, the fourth and fifth columns the g Co/cc and g Re/cc, respectively, and the sixth column the rim thickness or thickness of the outer metal shell in microns.

Catalysts Nos. 12–21, described in Table 3, were prepared to have metal shells or rims by use of a series of spray techniques. $TiO_2$ spheres were spread out on a wire screen and preheated in a vacuum oven at various temperatures. The hot spheres were removed from the oven, sprayed with a small amount of metal salt solution, and returned without delay to the oven where drying and partial decomposition of the cobalt nitrate salt occurred. The spraying sequence was repeated several times in order to impregnate a thin outer layer or rim of Co-Re onto the support. Preparative details are as follows:

Three solutions I, II and III, each constituted of a different solvent, and having specific concentrations of cobalt nitrate and perrhenic acid were employed in a series of spraying procedures. The three solutions are constituted as follows:

| Solution Number | Cobalt Nitrate Concentration g Co/ml | Perrhenic Acid Concentration g Re/ml | Solvent |
|---|---|---|---|
| I | 0.12 | 0.01 | 20% $H_2O$<br>80% Acetone |
| II | 0.12 | 0.03 | $H_2O$ |
| III | 0.12 | 0.01 | Acetone |

Five separate procedures, Procedures A, B, C, D and E, respectively, employing each of these three solutions, were employed to prepare catalysts, as follows:

A: 30 ml of Solution I added to 50 g $TiO_2$ spheres in 5 sprayings

B: 30 ml of Solution I added to 50 g $TiO_2$ spheres in 3 sprayings

C: 25 ml of Solution I added to 50 g $TiO_2$ spheres in 5 sprayings

D: 50 ml of Solution II added to 100 g $TiO_2$ spheres in 5 sprayings

E: 25 ml of Solution III added to 50 g $TiO_2$ spheres in 5 sprayings

Reference is made to Table 3. The procedure employed in spray coating the respective catalyst is identified in the second column of said table, and the $TiO_2$ pre-heat temperature is given in the third column of said table. The g Co/cc and g Re/cc of each catalyst is given in Columns 4 and 5, respectively, and the thickness of the catalyst rim is given in microns in the sixth column of the table.

The catalysts were diluted, in each instance, with equal volumes of $TiO_2$ or $SiO_2$ spheres to minimize temperature gradients, and the catalyst mixture then charged into a small fixed bed reactor unit. In preparation for conducting a run, the catalysts were activated by reduction with hydrogen at 450° C., at atmospheric pressure for one hour. Synthesis gas with a composition of 64% $H_{2-32}$% CO-4% Ne was then converted over the activated catalyst at 200° C. (or 220° C. for Catalyst No. 25), 280 psig for a test period of at least 20 hours. Gas hourly space velocities (GHSV) as given in each of the tables, represent the flow rate at 22° C. and atmospheric pressure passed over the volume of catalyst, excluding the diluent. Samples of the exit gas were periodically analyzed by as chromatography to determine the extent of CO conversion and the selectivity to methane, expressed as the moles of $CH_4$ formed per 100 moles of CO converted. Selectivity to $C_{4-}$ expressed as the wt % of $C_{4-}$ in the hydrocarbon product, was calculated from the methane selectivity data using an empirical correlation developed from data obtained in a small pilot plant. A productivity figure is also given for runs made with each of these catalysts, productivity being defined as the product of the values represented by the space velocity, the CO fraction in the feed and the fraction of the CO converted; the productivity being the volume CO measured at 22° C. and atmospheric pressure converted per hour per volume of catalyst.

TABLE 1

UNIFORMLY IMPREGNATED CATALYSTS, AND GAS CONVERSION RUNS MADE THEREWITH

| Catalyst Number | Wt. % g Co/cc | Wt. % g Rc/cc | GHSV | % Co Conv. | Produc-tivity | Mol. % $CH_4$ | Wt. % $C_{4-}$ |
|---|---|---|---|---|---|---|---|
| 1 | 0.0392 | 0.0034 | 200 | 67 | 43 | 5.4 | 9.4 |
| 2 | 0.0617 | 0.0046 | 750 | 50 | 120 | 10.5 | 16.9 |
| 3 | 0.1003 | 0.0080 | 500 | 80 | 128 | 11.1 | 17.7 |
| 4 | 0.0743 | 0.0056 | 750 | 64 | 154 | 11.5 | 18.3 |
| 5 | 0.0796 | 0.0050 | 750 | 71 | 170 | 13.1 | 20.7 |
| 6 | 0.1014 | 0.0084 | 750 | 77 | 185 | 13.9 | 21.8 |
| 7 | 0.0925 | 0.0066 | 750 | 77 | 185 | 13.9 | 20.9 |
| 8 | 0.1025 | 0.0068 | 1000 | 65 | 208 | 14.7 | 23.0 |

TABLE 2

RIM CATALYSTS PREPARED BY LIQUID DISPLACEMENT METHOD, AND GAS CONVERSION RUNS MADE THEREWITH

| Catalyst Number | Presoak Liquid | Displacement Time Minutes | g Co/cc | g Rc/cc | Rim Thickness Microns | GHSV | % CO Conv. | Productivity | Mol. % $CH_4$ | Wt. % $C_{4-}$ |
|---|---|---|---|---|---|---|---|---|---|---|
| 9 | 98% Mesitylene/ 2% n-Heptanol | 2 | 0.0264 | 0.0023 | 140(1) | 250 | 83 | 66 | 6.5 | 11.0 |
| 10 | 98% Mesitylene/ 2%-2-Ethyl-1-hexanol | 1 | 0.0373 | 0.0031 | 200(1) | 500 | 66 | 106 | 7.6 | 12.6 |
| 11 | 98% Mesitylene/ 2%-2-Ethyl-1-hexanol | 2 | 0.0459 | 0.0038 | 320(2) | 500 | 70 | 112 | 9.3 | 15.1 |

(1)The rim thickness of these catalysts falls within the acceptable range. An insufficient concentration of the total metals deposited on the $TiO_2$ spheres, however, is contained within the rim.
(2)Adequate metal concentration but large rim thickness lead to higher but still adequate methane and inadequate productivity.

TABLE 3

RIM CATALYSTS PREPARED BY SPRAYING METHOD, AND GAS CONVERSION RUNS MADE THEREWITH

| Catalysts Number | Procedure | $TiO_2$ Pre-Heat Temp. ° C. | g Co/cc | g Rc/cc | Rim Thickness Microns | GMSV | % Co Conv. | Productivity | Mol. % $CH_4$ | Wt. % $C_{4-}$ |
|---|---|---|---|---|---|---|---|---|---|---|
| 12 | A | 140 | 0.0624 | 0.0050 | 250 | 400 | 85 | 109 | 8.9 | 14.5 |
| 13 | B | 125 | 0.0818 | 0.0068 | 300 | 750 | 85 | 204 | 11.8 | 18.8 |
| 14 | C | 140 | 0.0531 | 00045 | 140 | 800 | 68 | 174 | 8.2 | 13.3 |
| 15 | C | 140 | 0.0613 | 0.0050 | 150 | 800 | 71 | 182 | 8.2 | 13.5 |
| 16 | C | 140 | 0.0739 | 0.0070 | 130 | 800 | 81 | 207 | 8.7 | 14.2 |
| 17 | D | 185 | 0.0507 | 0.0125 | 160 | 800 | 68 | 174 | 9.2 | 15.0 |
| 18 | E | 185 | 0.0549 | 0.0049 | 90 | 800 | 68 | 174 | 6.5 | 11.0 |
| 19 | C | 185 | 0.0483 | 0.0043 | 70 | 800 | 64 | 164 | 6.7 | 11.3 |
| 20 | C | 185 | 0.0474 | 0.0033 | 90 | 800 | 65 | 166 | 7.5 | 12.5 |
| 21 | C | 185 | 0.0603 | 0.0046 | 60 | 800 | 74 | 189 | 7.2 | 12.0 |

TABLE 4

CATALYSTS MADE FROM $SiO_2$ PARTICLES (2.5 MM DIA.) AND GAS CONVERSION RUNS THEREWITH

| Catalyst Number | Wt. % g Co/CC | Wt. % Re | Rim Thickness Microns | GHSV | % Co Conv. | Productivity | Mol. % $CH_4$ | wt % $C_{4-}$ |
|---|---|---|---|---|---|---|---|---|
| 22 | .133 | 2.4 | (1) | 600 | 71 | 136 | 19.5 | 30.0 |
| 23 | .035 | 0.4 | 118 | 400 | 67 | 86 | 5.7 | 9.8 |
| 24 | .067 | 1.5 | 192 | 800 | 71 | 182 | 13.4 | 21.9 |
| 25(2) | .067 | 1.5 | 192 | 1100 | 76 | 268 | 21.9 | 33.5 |

(1)Uniformly impregnated, no rim present
(2)Run at 220° C.

Figure 1:
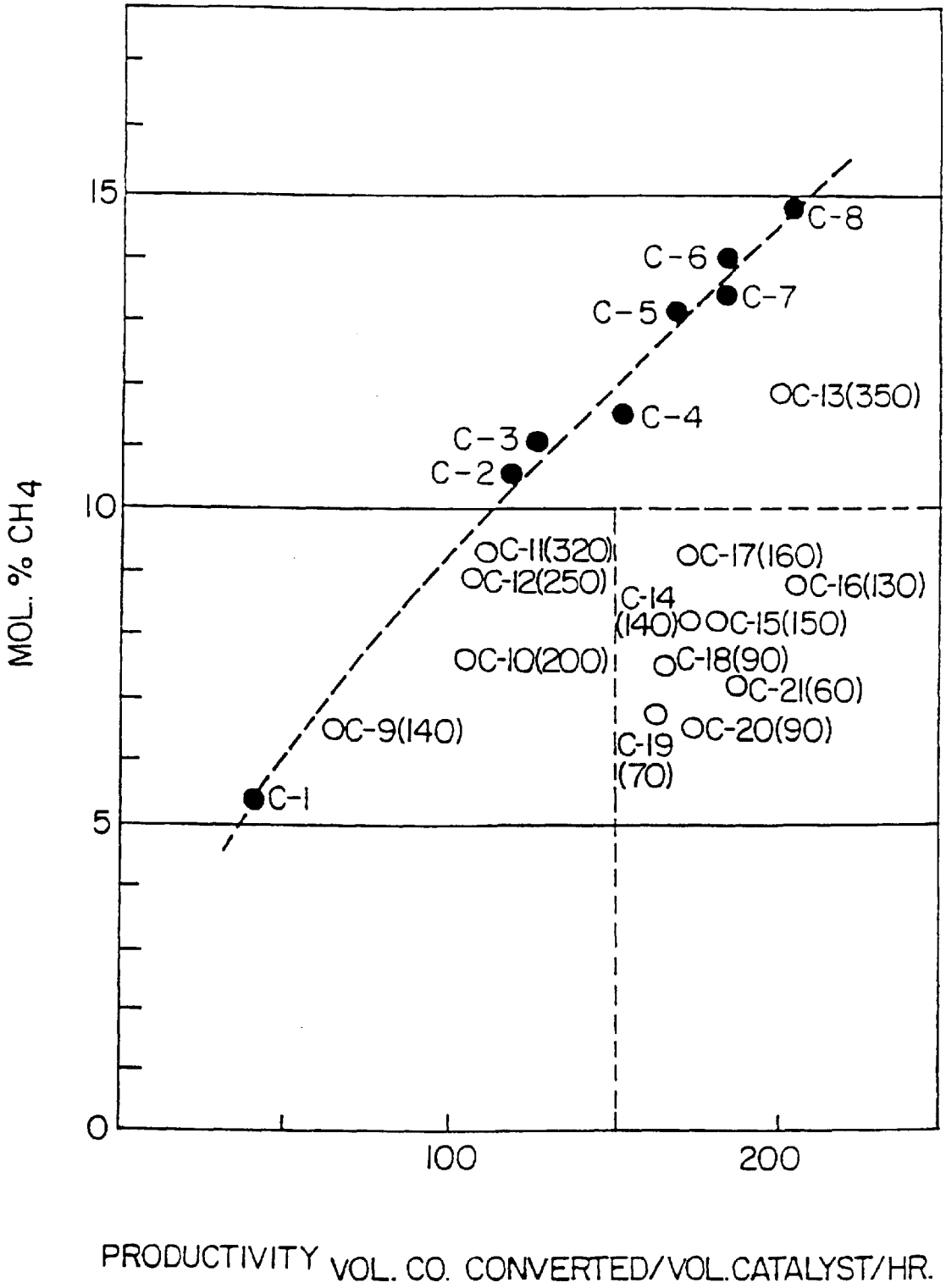
FIG. 1 is a plot of methane yield in the hydrocarbon synthesis product against productivity, vol. CO converted/ vol. catalyst/hr. The closed circles denote uniformly impregnated spheres; the open circles denote spheres impregnated only in the outer layer, the parenthetical number, indicating the thickness of the outer layer or rim.

The effectiveness of these catalysts for conducting synthesis gas reactions is best illustrated by comparison of the methane selectivity at given productivity with Catalysts 1–8 (Table 1), the catalysts formed by the uniform impregnation of the metals throughout the $TiO_2$ catalyst spheres, and Catalysts 9–11 (Table 2) and 12–21 (Table 3), those catalysts wherein the metals were deposited as a shell, or rim, upon the outside of the $TiO_2$ catalyst spheres. The same type of comparison is then made between certain of the latter class of catalysts, and others, which also differ one from another dependent upon the thickness of the metals-containing rim. These data are best graphically illustrated for ready, visual comparison. Reference is thus made to FIG. 1 wherein the methane selectivity produced at given productivity is plotted for each of the twenty-one catalysts described by reference to Tables 1–3. A solid black data point is plotted for each of Catalysts Nos. 1–8, formed from the uniformly impregnated $TiO_2$ spheres, and each data point is identified by catalyst number. An open circle is plotted for each data point representative of Catalysts Nos. 9–21, each is identified by catalyst number, and the rim thickness of the catalyst is given. The behavior of many of these catalysts (i.e., Catalysts 9–13), it will be observed is somewhat analogous to that of Catalysts Nos. 1–8. Catalysts Nos. 14–21, however, behave quite differently from either of the other groups of catalysts, i.e., Catalysts Nos. 1–8 or Catalysts 9–13. The methane selectivity is thus relatively low for Catalysts Nos. 9–12, but at the same time the productivities of these catalysts are quite low. On the other hand, the productivities of Catalysts Nos. 2–8 are higher than those of Catalysts Nos.

9–12, but at the same time these catalysts produce copious amounts of methane. In striking contrast to either of these groups of catalysts, Catalysts Nos. 14–21, all of which fall within the "box" depicted on the figure, provide very high productivities and, at the same time, low methane selectivities. Catalysts Nos. 14–21 thus differ profoundly from any of Catalysts Nos. 1–13 in their behavior, and in that the metals components of these catalysts is packed into a very thin rim, or shell, on the surface of the $TiO_2$ support.

These data thus show that a constant temperature as productivity increases so too does methane selectivity for both the groups of catalyst represented by Catalysts Nos. 1–8, the uniformly impregnated catalysts, and Catalysts Nos. 11–13 which have relatively thick outer shells or rims. Thus, methane selectivity increases in proportion to the metal loadings when the metals are dispersed throughout the support or carrier portion of the catalyst. Methane selectivity also increases in proportion to the thickness of the catalyst rim. Albeit the methane selectivities obtained with Catalysts Nos. 9–12 are within acceptable ranges, the productivities obtained with these catalysts are quite low. Catalyst No. 13 has adequate productivity but makes significant methane. Catalyst No. 9, although it has a thin metallic rim and provides low methane selectivity, its productivity is quite poor because of an insufficient loading of metals within the rim. Catalyst Nos. 14–21 which have thin metallic rims and relatively high metals loadings within the rims, on the other hand, provide low methane selectivities and high productivities.

The results observed with Catalyst Nos. 1–13 and 22 are consistent with the onset of a significant diffusion limitation at the higher productivities, which intensifies as the catalyst become more active. In sharp contrast, however, catalysts which have cobalt rim thicknesses of less than about 200 microns, notably from about 20 microns to about 180 microns, can produce at high productivities (i.e., at least about 150 $hr^{-1}$, or even at least about 200 $hr^{-1}$) very low methane selectivities. Catalysts with very thin rims counteract the diffusion problem by limiting reaction to the outer surface of the catalyst wherein lies the catalytically active metal components. The catalysts of this invention thus provide a means of operating at high productivity levels with low methane selectivities. Methane selectivities are reduced at higher and higher productivities, as the rim thickness is made smaller and smaller. When productivity is increased beyond 150 $hr^{-1}$, 200° C. to at least about 200 $hr^{-1}$ the metals rim should be no more than about 180 microns thick, and the rim can be even thinner. This region of operation, the best balance between activity and selectivity, is represented in FIGS. 1 and 2 by the area enclosed within the box formed by the dashed lines. FIG. 2 presents the performance of $SiO_2$ catalysts and Catalyst No. 24 illustrates this invention. The methane yield is slightly higher than for $TiO_2$ particles, owing to intrinsic qualities of $TiO_2$ catalysts. Nevertheless, the requirements for the best balance between productivity and selectivity are the same for $SiO_2$ catalysts as for $TiO_2$ catalysts, e.g., adequate metal loading in a relatively thin rim. Catalyst No. 23, although it has a thin rim and provides low methane selectivity, its productivity is quite poor because of an insufficient loading of metals within the rim. FIG. 2 also includes calculated numbers on productivity from a EPA 178008 based on a 2.5 mm particle all of which shown unacceptably high levels of methane yield because of the relatively thick rims encountered in that case.

These data further show that the catalysts of this invention (Catalyst Nos. 14–21 and 24) can be readily prepared by the process of sequentially, or repetitively spraying hot, or preheated support particles with solutions containing compounds or salts of the metals. Suitably, the $TiO_2$ or $SiO_2$ substrate is preheated to temperatures of at least about 140° C. to about 185° C., prior to or at the time of contact thereof with the solution. Higher temperatures can be employed, but temperatures below about 140° C. do not produce a sufficiently thin rim of the metals on the catalyst support. The repetitive spraying technique is shown to be superior to liquid displacement technique used to prepare Catalyst Nos. 9–10 and 23 wherein only low cobalt loadings were deposited in a single contact because of the cobalt concentration limit in the displacing solution. Longer displacement time increases the metal loading but produces a thicker rim as shown by Catalyst No. 11 compared with Catalyst No. 10. The spray technique provides especially good dispersion of the metals as a thin rim at the outer surface of the support particles by application of the metals a little at a time by multiple impregnations. Loading the metals onto the catalysts in this manner increases the activity of the catalysts and provides higher productivity.

These reactions can be conducted with the catalysts of the present invention in any Fischer-Tropsch reactor system, e.g., fixed bed, fluidized bed, or other reactors, with or without the recycle of any unconverted gas and/or liquid product. The $C_{10+}$ product that is obtained is an admixture of linear paraffins and olefins which can be further refined and upgraded to high quality middle distillate fuels, or such other products as mogas, diesel fuel, jet fuel and the like. A premium grade middle distillate fuel of carbon number ranging from about $C_{10}$ to about $C_{20}$ can also be produced from the $C_{10+}$ hydrocarbon product. The catalyst is constituted of cobalt supported on a carrier, preferably titania, and especially cobalt supported on a rutile form of $TiO_2$ or rutile-titania-containing support which can contain other materials such as $SiO_2$, MgO, $ZrO_2$, $Al_2O_3$. The catalyst is preferably reduced with a $H_2$-containing gas at start-up.

EXAMPLE 9

About 14,500 lbs of finished catalyst was obtained by double impregnating a spray-dried support made from Degussa P-25 titania. The titania was spray-dried with an alumina sol binder. Product with an average particle size of about 45 microns was made in very high yield (97%). The support was then converted into the rutile form by calcination at high temperature in a 30"×50" rotary calciner. Impregnation with an aqueous solution of cobalt nitrate and perrhenic acid was performed batch-wise in a 5 $ft^3$ V-blender. The nitrate salt was decomposed by calcining the catalyst in the larger rotary at about 450° C. A second pass through impregnation and calcination produced the finished catalyst.

High resolution imaging and EDS analysis of a cross-sectional view of the above catalyst is shown in FIG. 3.

It is apparent that various modifications and changes can be made without departing the spirit and scope of the present invention.

What is claimed is:

1. A process useful for the conversion of synthesis gas to liquid hydrocarbons and less than about 10 mole % methane which comprises contacting at reaction conditions a feed comprised of carbon monoxide and hydrogen, in $H_2$:CO molar ratio equal to or greater than about 0.5:1 at total pressure equal to or greater than about 80 psig, over a catalyst composition having a productivity of at least 150 $hr^{-1}$ at 200° C. and which comprises cobalt dispersed as a catalytically active layer upon the outer surface of an inorganic oxide support of a thickness of less than about 200 microns, with the loading of cobalt at least about 0.04 g/cc in said catalytically active layer, calculated as metallic cobalt per packed bulk volume of catalyst.

2. The process of claim 1 wherein the molar ratio of $H_2$:CO ranges from about 1.7:1 to about 2.5:1.

3. The process of claim 2 wherein the total pressure of the reaction ranges from about 140 psig to about 400 psig.

4. The process of claim 1 wherein the reaction conditions are defined within ranges as follows:

| | |
|---|---|
| $H_2$:CO mole ratio | about 1.7:1 to 2.5:1 |
| Gas Hourly Space Velocities, V/Hr/V | about 300 to 1500 |
| Temperature, ° C. | about 190 to 220 |
| Total Pressure, psig | about 140 to 400 |

5. The process of claim 1 wherein the catalytically active surface layer of the catalyst is of average thickness ranging from about 5 microns to about 200 microns with the cobalt loading ranging being at least about 0.04 g/cc in said catalytically active surface layer.

6. The process of claim 1 wherein the catalyst further comprises rhenium rhenium constitutes part of the catalytically active surface layer of the catalyst.

7. The process of claim 1 wherein the catalyst further comprises hafnium which constitutes part of the catalytically active surface layer of the catalyst.

8. The process of claim 1 wherein the support is comprised of silica or titania.

9. A process for the conversion of synthesis gas to $C_{10+}$ hydrocarbons which comprises contacting at reaction conditions a feed comprised of an admixture of carbon monoxide and hydrogen, in $H_2$:CO molar ratio equal to or greater than about 1.71 at total pressure equal to or greater than about 80 psig, over a catalyst composition which comprises cobalt dispersed as a catalytically active layer upon the outer surface of a silica or titania containing support, said active layer being of a thickness of less than 200 microns, and with sufficient cobalt loading to produce a productivity of at least about 150 $hr^{-1}$ at 200° C. and convert to methane less than 10 mole percent of the carbon monoxide converted.

10. The process of claim 9 wherein the support is comprised predominantly of silica.

11. The process of claim 1 wherein said process is a slurry-bed synthesis gas conversion process and said catalyst having a particle size diameter of about 10 microns to about 1 mm.

*12. The process of claim 1 wherein said liquid hydrocarbon comprises a high quality distillate fuel.*

*13. The process of claim 1 wherein said liquid hydrocarbon comprises $C_{10+}$ hydrocarbons.*

*14. The process of claim 13 wherein said $C_{10+}$ hydrocarbons comprise $C_{10+}$ linear paraffins.*

*15. The process of claim 13 comprising the further step of producing a middle distillate fuel from said $C_{10+}$ hydrocarbons.*

*16. The process of claim 15 wherein said middle distillate fuel comprises a diesel fuel.*

*17. The process of claim 15 wherein said middle distillate fuel comprises a $C_{10}$–$C_{20}$ product.*

*18. The process of claim 15 wherein said middle distillate fuel comprises a jet fuel.*

*19. The process of claim 13 including upgrading said $C_{10+}$ hydrocarbons.*

*20. The process of claim 19 including upgrading said $C_{10+}$ hydrocarbons to a diesel fuel.*

*21. The process of claim 19 including upgrading said $C_{10+}$ hydrocarbons to a jet fuel.*

*22. The process of claim 9 wherein said $C_{10+}$ hydrocarbons comprise $C_{10+}$ linear paraffins.*

*23. The process of claim 9 comprising the further step of producing a middle distillate fuel from said $C_{10+}$ hydrocarbons.*

*24. The process of claim 23 wherein said middle distillate fuel comprises a diesel fuel.*

*25. The process of claim 23 wherein said middle distillate fuel comprises a jet fuel.*

*26. The process of claim 23 wherein said middle distillate fuel comprises a $C_{10}$–$C_{20}$ product.*

*27. The process of claim 9 including upgrading said $C_{10+}$ hydrocarbons.*

*28. The process of claim 27 including upgrading said $C_{10+}$ hydrocarbons to a diesel fuel.*

*29. The process of claim 27 including upgrading said $C_{10+}$ hydrocarbons to a jet fuel.*

* * * * *

Disclaimer

Re. 37,406—William C. Behrmann; Kym B. Arcuri; Charles H. Mauldin, all of Baton Rouge, LA. SURFACE SUPPORTED COBALT CATALYSTS, PROCESS UTILIZING THESE CATALYSTS FOR THE PREPARATION OF HYDROCARBONS FROM SYNTHESIS GAS AND PROCESS FOR THE PREPARATION OF SAID CATALYSTS. Patent dated October 9, 2001. Disclaimer filed February 27, 2002 by the assignee, Exxon Research and Engineering Co.

The term of this patent shall not extend beyond the expiration date of Pat. No. 5,128,377.

*(Official Gazette, August 13, 2002)*